United States Patent [19]

Yamada

[11] 4,290,776
[45] Sep. 22, 1981

[54] METHOD FOR ANALYZING ACIDIC SUBSTANCES BY HIGH SPEED LIQUID CHROMATOGRAPHY

[75] Inventor: Tsuyoshi Yamada, Yokohama, Japan

[73] Assignee: Showa Denko Kabushiki Kaisha, Tokyo, Japan

[21] Appl. No.: 160,647

[22] Filed: Jun. 18, 1980

Related U.S. Application Data

[63] Continuation of Ser. No. 98,812, Nov. 30, 1979, abandoned.

[30] Foreign Application Priority Data

Dec. 6, 1978 [JP] Japan .................................. 53/149917

[51] Int. Cl.³ .............................................. B01D 15/08
[52] U.S. Cl. .................................. 23/230 R; 210/635; 210/659
[58] Field of Search ................ 210/198 C, 659, 656, 210/635; 23/230 R, 230 M

[56] References Cited

U.S. PATENT DOCUMENTS

| | | | |
|---|---|---|---|
| 3,892,530 | 1/1975 | Felix | 23/230 M |
| 3,997,298 | 12/1976 | McLafferty | 210/198.2 |
| 4,039,284 | 8/1977 | Mancini | 23/230 M |
| 4,073,725 | 2/1978 | Takeuchi | 210/198.2 |
| 4,137,161 | 1/1979 | Shimada et al. | 210/198.2 |

OTHER PUBLICATIONS

A Highly Efficient Carboxylic Acid Analyzer and Its Application by Nakajima et al., in Journal of Chromatography 123 (1976), 129–138.
Design of a High Efficiency Liquid Chromatograph Using Specific Detection and Its Evaluation for Analysis of Tricarboxylic Acid Cycle (TCA) Intermediates and Related Compounds on a Nano-Equivalent Scale by Stahl et al. in Journal of Chromatography Science, vol. 10, (Feb. 1972), pp. 95–102.

*Primary Examiner*—John Adee
*Attorney, Agent, or Firm*—Armstrong, Nikaido, Marmelstein & Kubovcik

[57] ABSTRACT

Provided is a process for analyzing acidic substances by high speed liquid chromatography. An aqueous pH indicator solution is incorporated in an effluent from a column packed with a packing material, and the pH indicator-incorporated effluent is monitored by means of spectrophotometry. As the pH indicator, a sulphon phthalein indicator is used, which is at least slightly soluble in water and has a pH transformation range falling within the pH range of from about 3.0 to about 10.0 and which exhibits, when maintained at a pH lower than the pH transformation range, the minimum transmittance at a wave length of about 420–440 nm and, when maintained at a pH higher than the pH transformation range, the minimum transmittance at a wave length of at least about 558 nm. The packing material is preferably a sulfonated styrene/divinylbenzene copolymer having a total exchange capacity of about 4 to 5 milli-equivalent/gram.

4 Claims, 6 Drawing Figures

METHOD FOR ANALYZING ACIDIC SUBSTANCES BY HIGH SPEED LIQUID CHROMATOGRAPHY

This is a continuation of application Ser. No. 098,812, filed Nov. 30, 1979, now abandoned.

BACKGROUND OF THE INVENTION (1) Field of the Invention

This invention relates to a method for analyzing acidic substances, particularly organic acidic substances, by high speed liquid chromatography.

(2) Description of the Prior Art

Many apparatuses for detecting organic acidic substances by high speed liquid chromatography have been heretofore proposed and put to practical use. These apparatuses have, arranged in series along the path of flow, an eluent supply means comprising an eluent receptacle and a high pressure metering pump; a specimen material supply means comprising a specimen material injector; a column packed with a packing material; and a detector. Many types of detectors are known such as a differential refractometer, a photospectrometer, a thermal detector, a conductivity meter and a solute transport detector. The conventional apparatuses provided with these detectors possess both merits and demerits in analysis properties such as detecting sensibility, universability, selectivity and speed of response.

It is also known to combine a spectrophotometer with a color producing system. For example, a color producing system utilizing dicyclohexyl carbodiimide (DCC), which develops a purplish red color (500–550 nm) under certain conditions, is arranged along the path of flow between the column device and the spectrophotometer-provided detector. This analyzing apparatus exhibits good selectivity and detecting sensibility. However, the color development of DCC involves sequence reactions and, therefore, a plurality of reagent delivery means must be arranged. Thus, the analyzing apparatus is complex and a substantial period of time is necessary for the analysis.

Another example of the combination of a spectrophotometer with a color producing system is described in K. W. Stahl et al: Journal of Chromatographic Science, vol. 10, pages 95–102 (February, 1972). In this color producing system, o-nitrophenol pH indicator is used. Furthermore, an organic solvent is used as the eluent and silica gel is used as the packing material. The o-nitrophenol pH indicator exhibits a visible spectrum such that the areas defined by the convex lines of the transmittance spectrum as measured in alkaline and acidic media overlap with each other to a great degree. Therefore, the o-nitrophenol pH indicator exhibits a poor sensibility when measured on an acidic side. Furthermore, the silica gel used must be treated with sulfuric acid prior to the passage of the eluent through the column. It is difficult or even impossible to completely avoid contamination of the effluent with a trace amount of the remaining sulfuric acid. This unavoidable contamination also reduces the sensibility of the pH indicator and the reproducibility.

SUMMARY OF THE INVENTION

It is, therefore, the main object of the present invention to provide a method for analyzing acidic substances by high speed liquid chromatography which provides satisfactory detecting sensibility, selectivity and response speed of the analysis.

Other objects and advantages of the present invention will be apparent from the following description.

In accordance with the present invention, there is provided a method utilizing an apparatus for analyzing acidic substances by high speed liquid chromatography which apparatus comprises, arranged in series along the path of flow, an eluent supply means, a specimen material supply means, a column packed with a packing material and a detecting means having a spectrophotometer; characterized by being provided with a pH indicator supply means arranged along the path of flow between the column and the detecting means; said pH indicator being a sulphonphthalein indicator which is at least slightly soluble in water and has a pH transformation range falling within the pH range of from about 3.0 to about 10.0 and which exhibits, when maintained at a pH lower than the pH transformation range, the minimum transmittance at a wave length of about 420–440 nm and, when maintained at a pH higher than the pH transformation range, the minimum transmittance at a wave length of at least about 558 nm.

BRIEF DESCRIPTION OF THE DRAWINGS

The invention will be described with reference to the accompanying drawings wherein.

DESCRIPTION OF THE PREFERRED EMBODIMENTS

Figure 1:
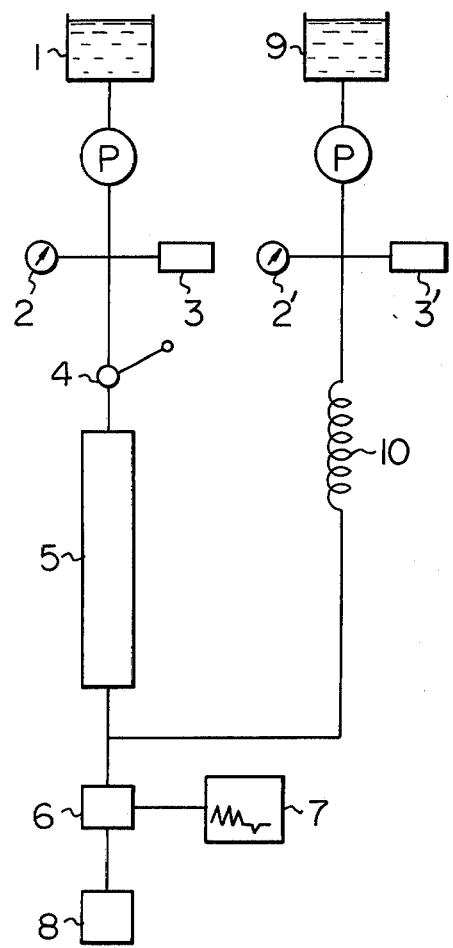
FIG. 1 is a block diagram of the analyzing apparatus of the invention.

Referring to FIG. 1, an eluent is supplied at a constant feed rate by a high pressure metering pump P from a tank 1 to a separation column 5. A specimen material is injected into the flow of the eluent by an injecting device 4 located upstream to the separation column 5. The liquid pressure is measured by a pressure gauge 2. The pressure damper 3 controls the fluctuation of the flow rate caused by the pulsation of the pump P. An aqueous dilute solution of a sulphonphthalein indicator is supplied by a metering pump P from a reservoir 9 through a resistance tube 10 to the point where the indicator solution is joined with the effluent flowing from the separation column 5. The resistance tube 10 may be made of a fine tube or filled with quartz powder. The reference numerals 2' and 3' indicate a pressure gauge and a pressure damper, respectively. The effluent flowing from the separation column 5 and having the indicator solution joined therewith is analyzed by a detector 6 provided with a spectrophotometer. That is, the absorbance of the effluent is measured by the spectrophotometer. The chromatogram is recorded by a recording device 7. The reference numeral 8 indicates a waste reservoir.

The pH indicator used is a sulphonphthalein which is at least slightly soluble in water. The sulphonphthalein indicator should be soluble in water at least to an extent such that the color change of the aqueous solution can be visually recognized. The sulphonphthalein indicator Preferable sulphonphthalein indicators are listed in Table I, below.

TABLE I

| Common name | Chemical name | Structure A | Structure B | Structure C | PH transformation range | Color change Acid-Alk. (w.l. *2,*3) |
|---|---|---|---|---|---|---|
| Bromophenol blue | Tetrabromo-phenol-s.*1 | H | Br | Br | 3.0–4.6 | Y - P (592) |
| Bromochloro-phenol blue | Dibromodichloro-phenol-s. | H | Cl | Br | 3.2–4.8 | Y - B |
| Bromocresol green | Tetrabromo-m-cresol-s. | CH$_3$ | Br | Br | 3.8–5.4 | Y - B (617) |
| Chlorophenol red | Dichloro-phenol-s. | H | Cl | H | 4.8–6.4 | Y - R (573) |
| Bromophenol red | Dibromo-phenol-s. | H | Br | H | 5.2–6.8 | Y - R (574) |
| Bromocresol purple | Dibromo-o-cresol-s. | H | Br | CH$_3$ | 5.2–6.8 | Y - P (591) |
| | Dichloro-o-cresol-s. | H | Cl | CH$_3$ | | |
| Bromothymol blue | Dibromo-thymol-s | CH$_3$ | Br | CH—(CH$_3$)$_2$ | 6.0–7.6 | Y - B (617) |
| Phenol red | Phenol-s. | H | H | H | 6.4–8.2 | Y - R (558) |
| Cresol red | o-Cresol-s. | H | CH$_3$ | H | 7.0–8.8 | Y - R (572) |
| m-Cresol purple | m-Cresol-s. | CH$_3$ | H | H | 7.4–9.0 | Y - P (580) |
| p-Xylenol blue | p-Xylenol-s. | CH$_3$ | H | CH$_3$ | 8.0–9.6 | Y - B |
| Thymol blue | Thymol-s. | CH$_3$ | H | CH—(CH$_3$)$_2$ | 8.0–9.6 | Y - B (596) |

*1 -s. = -sulphonphthalein
*2 w.l. = wave length in nm at which the minimum transmittance appears as measured on the alkaline side
*3 Y = yellow, P = purple, B = blue and R = red should preferably be such that, when its aqueous solution is mixed with the eluent used, the sulphonphthalein indicator does not precipitate. The sulphonphthalein indicator should have a pH transformation range falling within the pH range of from about 3.0 to about 10.0. Furthermore, the sulphonphthalein indicator should exhibit, when maintained at a pH lower than the pH transformation range, the minimum transmittance at a wave length of about 420–440 nm, and, when maintained at a pH higher than the pH transformation range, the minimum transmittance at a wave length of at least about 558 nm.

The sulphonphthalein indicators having the above-mentioned characteristics include, for example, those which are represented by the formula:

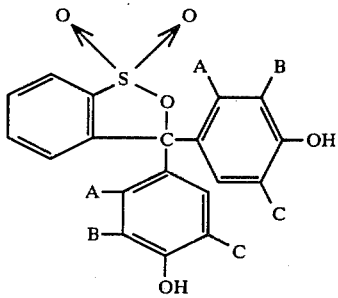

wherein A, B and C are as follows:
(1) A=H, B=H and C=H,
(2) One of A and B is CH$_3$, the other =H and C=H,
(3) A=CH$_3$, B=H and C=CH$_3$ or CH(CH$_3$)$_2$,
(4) A=H, B=Cl or Br and C=H or CH$_3$,
(5) A=CH$_3$, B=Br and C=Br or CH(CH$_3$)$_2$, and
(6) A=H, B=Br and C=Cl or Br.

Figure 2:
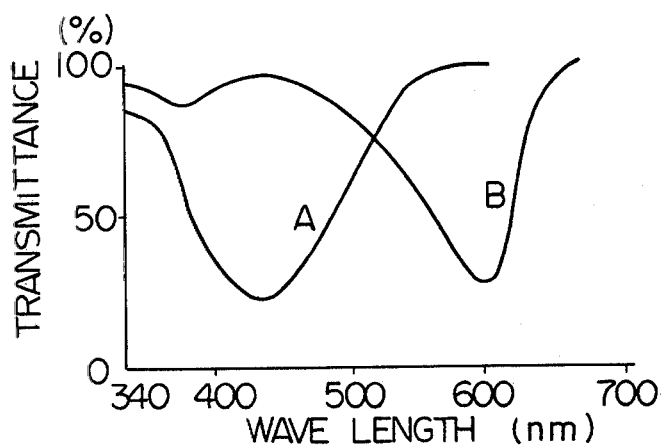
FIG. 2 is a visible spectrum of bromocresol purple.

Most preferable sulphonphthalein indicators are bromocresol purple and bromothymol blue. These sulphonphthalein indicators exhibit, as compared with other sulphonphthalein indicators, the difference between the wave length at which the minimum transmittance appears as measured on the alkaline side and the wave length at which the minimum transmittance appears as measured on the acidic side is relatively large. The visible spectrum of an aqueous bromocresol purple solution is shown in FIG. 2 wherein the ordinate and the abscissa represent the transmittance in % and the wave length in nm, respectively. The transmittance curves A and B are obtained as measured on the acidic side (pH<5.2) and the alkaline side (pH>6.8), respectively.

Among the pH indicators other than the sulphonphthalein indicators, the following can also be used although they are not preferable.

| Name | Chemical formula | PH transformation range | Color change |
|---|---|---|---|
| Congo red | C$_{32}$H$_{22}$N$_6$O$_6$S$_2$Na | 3.0–5.0 | B - R |
| Methyl orange | C$_{14}$H$_{14}$N$_3$NaO$_3$S | 3.1–4.4 | R - Y |
| Sodium alizarin-sulfonate | C$_6$H$_4$(CO)$_2$C$_6$H(OH)$_2$SO$_3$Na | 3.7–5.2 | Y - P |
| Indo-oxime | C$_{18}$H$_{10}$N$_3$NaO$_2$ | 6.0–8.0 | R - B |

A preferable packing material to be packed in the separation column is cross-linked sulfonated styrene/-divinylbenzene copolymers. When the sulfonated styrene/divinylbenzene copolymer packing material is used, an acidic solution such as an about 0.02% aqueous solution of perchloric acid or phosphoric acid may preferably be used as the eluent. Accordingly, it is preferable that the aqueous sulphonphthalein indicator solution used be slightly alkaline so that, when the sulphonphthalein indicator solution is incorporated with the effluent from the column, the resulting effluent is slightly acidic. The aqueous sulphonphthalein indicator solution preferably contains from about 0.00005 to 0.001 mole/liter of the indicator and from about 0.001 to 0.1 mole/liter of a buffer. The buffer used varies depending upon the pH transformation range of the indicator used. Usually, the following buffers may be used.

| PH transformation range | Buffer |
|---|---|
| About 3.0~6.0 | Sodium acetate |
| About 5.0~8.0 | Sodium hydrogenphosphate |
| About 7.0~10.0 | Sodium tertiary phosphate |

Depending upon the pH transformation range of the indicator used, sodium acetate may be used in combination with acetic acid, and sodium hydrogenphosphate may be used in combination with sodium tertiary phosphate. If the concentration of acid in the eluent is raised, a corresponding amount of an alkali such as sodium hydroxide may be incorporated in the pH indicator solution. When the above-specified sulphonphthalein indicator is used under the above-mentioned conditions, and the absorbance of the effluent is measured by applying a monochromatic light of a wave length of about 420 to 440 nm, an acidic specimen material of a very low concentration, e.g., one ppm, can be detected. And, the selectivity for acidic substances is satisfactorily large.

As mentioned above, a preferable packing material is crosslinked sulfonated styrene/divinylbenzene copolymers, particularly those which contain about 10% by weight of units derived from divinylbenzene and have a total exchange capacity of about 4 to 5 milliequivalent/gram. The shape of the packing material is not critical but preferably should be spherical.

An example of such packing material is Shodex Ionpak C-811 (trade name, supplied by Showa Denko K.K., Japan) which is a sphere of 12.5±5 μm in diameter and has an exclusion displacement limit corresponding to dextran having a molecular weight of about 1,000 and has a bed volume of about 3 ml/g in water. The crosslinked sulfonated styrene/divinylbenzene copolymers are advantageous because they make it possible to shorten the analyzing period. The analyzing period of the apparatus of the invention is usually about 20 to 40 minutes, whereas the analyzing period of the conventional apparatus provided with a detector utilizing the color development of DCC is about two hours. Another advantage of the crosslinked sulfonated styrene/divinylbenzene copolymers is that the packing material is relatively stiff and exhibits good resistance to external force and chemicals, and therefore, its maintenance is not troublesome.

The eluent tank, the metering pumps, the pressure dampers, the specimen material injecting device and the detector provided with a photospectrometer may be conventional. It is preferable that, in order to mix uniformly the effluent from the column and the pH indicator solution, the tube arranged between the joining point at which the effluent and the pH indicator solution join together and the detector be packed with twisted wires so that the effluent and the pH indicator solution are forced through the spaces between the wires.

The apparatus of the invention is useful for analyzing organic acids. Particularly, it is used for determining the concentration of or identifying organic acids in fruit drinks, refreshing drinks and other beverages. It can also be used for analyzing urine and blood.

Working examples wherein the apparatus of the invention is used for determining organic acids are given below.

EXAMPLE 1

A waste molasses, which was produced in a sugar refining process and contained citric acid (1), malic acid or malonic acid (2), succinic acid (3), glycolic acid (4), lactic acid (5), formic acid (6), acetic acid (7), sucrose (a), dextrose (b) and D-fructose (c), was analyzed by using the apparatus having the arrangement illustrated in FIG. 1. The analyzing conditions were as follows.

Aqueous pH indicator solution: Bromocresol purple 0.0002 mole/liter, $Na_2HPO_4$ 0.008 mole/liter, Flow rate 1.0 ml/min.

Eluent: Aqueous 0.02% $HClO_4$ solution, Flow rate 1 ml/min, feed pressure 15 kg/cm$^2$.

Column: Shodex Ionpak C-811, temperature 63° C.

Figure 3A:
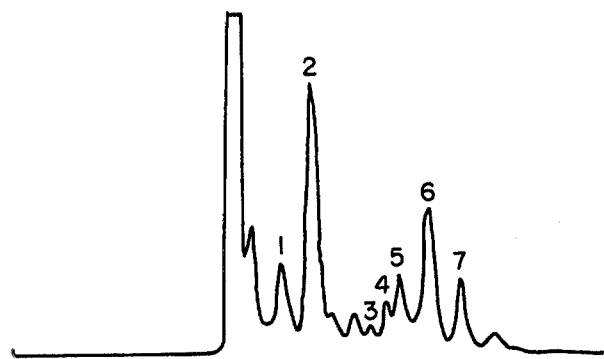
FIGS. 3A–3B are chromatograms of waste molasses produced in a sugar refining process, which chromatograms are obtained by using a bromocresol purple pH indicator.

Detector: Wave length 430 nm. The chromatogram obtained is shown in FIG. 3A.

Figure 3B:
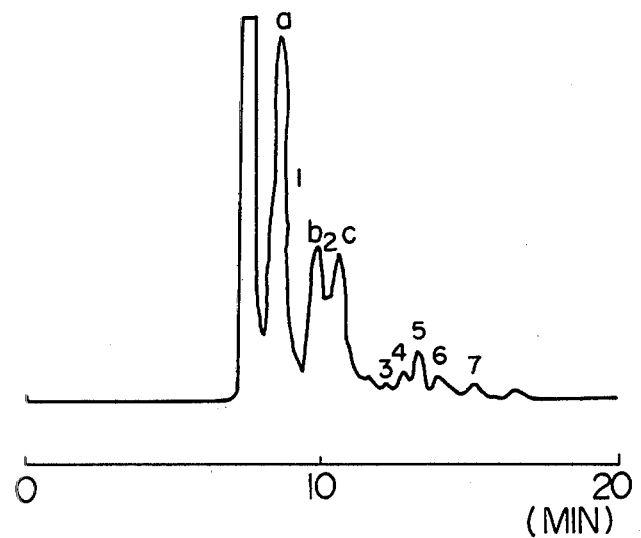

For comparison purposes, a waste molasses similar to that used above was analyzed by a conventional analyzing apparatus which was similar to that used above except that it was provided with a differential refractometer in place of the combination of the photospectrometer with the pH indicator system. The analyzing conditions were substantially the same as those explained above. The chromatogram obtained is shown in FIG. 3B. The reference numerals and letters in FIG. 3 correspond to the organic acids and the sugar, listed above. As can be seen from FIG. 3, when a differential refractometer is used, peaks corresponding to the sugar (a, b and c) appear in the early stage, and thus, it is difficult to analyze some of the organic acids, such as citric acid and malic acid, which peaks also appear in the early stage. In contrast, when the apparatus of the invention is used, peaks of all organic acids appear distinctly.

EXAMPLE 2

An artificial mixture comprised of oxalic acid (1), citric acid (2), malic acid (3), succinic acid (4), formic acid (5), acetic acid (6), propionic acid (7), isobutyric acid (8), n-butyric acid (9), pivalic acid (10), isovaleric acid (11) and n-valeric acid (12), each having a concentration of 200 ppm was tested by using the same apparatus (provided with the photospectrometer) as that employed in Example 1. The testing conditions were as follows.

Amount of specimen solution: 200 μl,

Aqueous pH indicator solution: Bromothymol blue 0.0002 mole/liter, $Na_2HPO_4$ 0.01 mole/liter, Flow rate 1.5 ml/min., Eluent: Aqueous 0.02% $HClO_4$ solution, Flow rate 1.5 ml/min., Feed pressure 20 kg/cm$^2$, Column: Shodex Ionpak C-811, room temperature, Detector: Wave length 440 nm, Absorbance 0.4.

Figure 4:
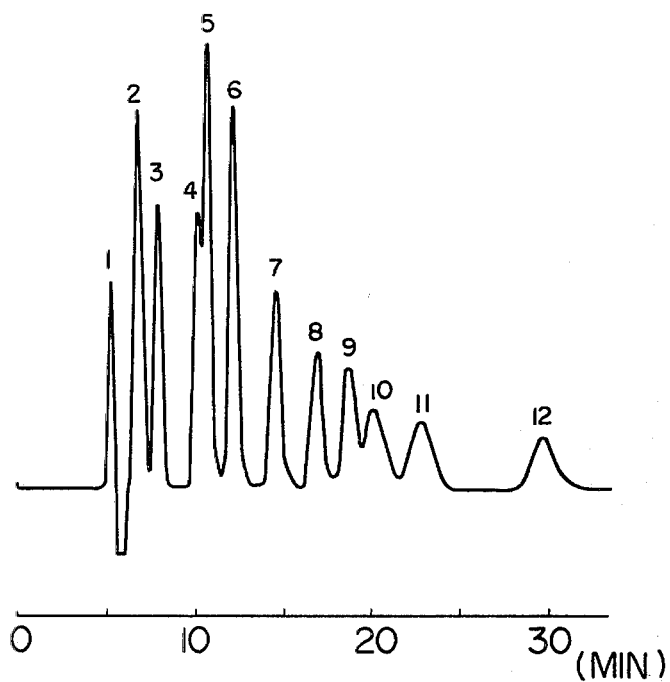
FIG. 4 is a chromatogram of an artificial mixture of twelve carboxylic acids obtained by using a bromothymol blue pH indicator; and, FIG. 5 is a chromatogram of an aqueous malonic acid solution obtained by using a cresol red pH indicator.

The chromatogram obtained is shown in FIG. 4. The reference numerals correspond to the organic acids, listed above.

EXAMPLE 3

An aqueous malonic acid solution having a concentration of 200 μl was tested by using the same apparatus (provided with the photospectrometer) as that employed in Example 1. The testing conditions were as follows.

Amount of specimen solution: 200 μl,

Aqueous pH indicator solution: Cresol red 0.0008 mole/liter, Na₃PO₄ 0.02 mole/liter, Flow rate 0.73 ml/min., Fluent: Aqueous 0.1% HClO₄ solution, Flow rate 1.0 ml/min., Feed pressure 15 kg/cm², Column: Shodex Ionpak C-811, temperature 63° C.

Detector: Wave length 430 nm, Absorbance 1.28.

Figure 5:
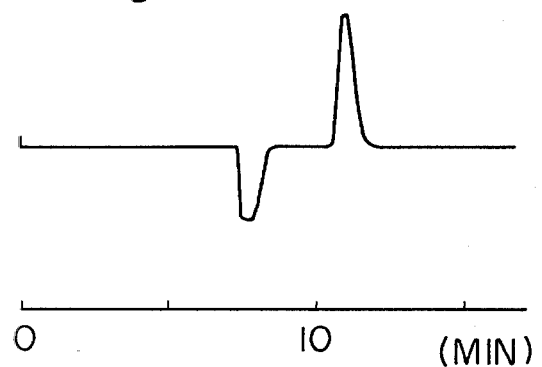

The chromatogram obtained is shown in FIG. 5, wherein the downward peak corresponds to the water medium used.

What I claim is:

1. An improvement in a process for analyzing acidic substances by high speed liquid chromatography which comprises incorporating an aqueous pH indicator solution in an effluent from a column packed with a packing material, and monitoring the pH indicator-incorporated effluent by means of spectrophotometry; the improvement comprising using as the pH indicator a sulphonphthalein indicator which is at least slightly soluble in water and has a pH transformation range falling within the pH range of from about 3.0 to about 10.0 and which exhibits, when maintained at a pH lower than the pH transformation range, a minimum transmittance at a wave length of about 420–440 nm and, when maintained at a pH higher than the pH transformation range, a minimum transmittance at a wave length of at least about 558 nm.

2. A process according to claim 1 wherein said sulphonphthalein indicator is represented by the formula:

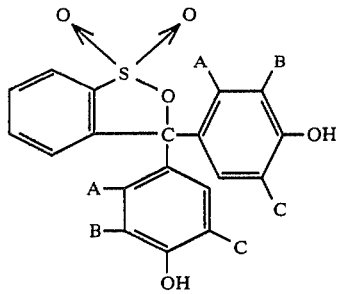

wherein A, B and C are as follows:
   (1) A=H, B=H and C=H,
   (2) One of A and B is CH₃, the other =H and C=H,
   (3) A=CH₃, B=H and C=CH₃ or CH(CH₃)₂,
   (4) A=H, B=Cl or Br and C=H or CH₃,
   (5) A=CH₃, B=Br and C=Br or CH(CH₃)₂, or
   (6) A=H, B=Br and C=Cl or Br.

3. A process according to claim 1 or 2 wherein the pH indicator is used in an aqueous solution containing from about 0.00005 to about 0.001 mole/liter of the pH indicator and from about 0.001 to 0.1 mole/liter of a buffer.

4. A process according to claim 1 or 2 wherein the packing material is a sulfonated styrene/divinylbenzene copolymer having a total exchange capacity of about 4 to 5 milli-equivalent/gram.

* * * * *